United States Patent [19]
Dinkler

[11] Patent Number: 5,537,704
[45] Date of Patent: Jul. 23, 1996

[54] RADIOLUCENT HEAD CLAMP

[75] Inventor: Charles Dinkler, Cincinnati, Ohio

[73] Assignee: Ohio Medical Instrument Company, Inc., Cincinnati, Ohio

[21] Appl. No.: 276,915

[22] Filed: Jul. 19, 1994

[51] Int. Cl.⁶ ................................................. A61G 13/00
[52] U.S. Cl. ..................... 5/622; 5/640; 5/643; 602/33; 602/37
[58] Field of Search .............................. 5/622, 637, 640, 5/643; 602/32, 33, 35, 36, 37

[56] References Cited

U.S. PATENT DOCUMENTS

| | | |
|---|---|---|
| 3,835,861 | 9/1974 | Kees, Jr. et al. . |
| 4,169,478 | 10/1979 | Hickmann . |
| 5,254,079 | 10/1993 | Agbodoe et al. . |
| 5,269,034 | 12/1993 | Day et al. . |
| 5,276,927 | 1/1994 | Day . |
| 5,318,590 | 6/1994 | Agbodoe ................................ 5/637 X |

Primary Examiner—Michael F. Trettel
Attorney, Agent, or Firm—Wood, Herron & Evans

[57] ABSTRACT

A radiolucent head clamp having a C-shaped frame with a fixed head-engaging pin on one side and a pair of head-engaging pins on the opposite side. The opposite side of the clamp has a radiolucent rotation mechanism for adjusting the angular position of the pair of head-engaging pins and a radiolucent translation mechanism for linearly moving the pair of head-engaging pins with respect to the fixed head-engaging pin.

10 Claims, 3 Drawing Sheets

RADIOLUCENT HEAD CLAMP

BACKGROUND OF THE INVENTION

This invention relates to a head clamp principally for use with radiological procedures and more particularly to a radiolucent head clamp having mechanisms for axially and rotationally adjusting the head-engaging pins of a head clamp, from a single side of the clamp.

An example of a head clamp with a single side control is shown in the Day, et al. U.S. Pat. No. 5,269,034, assigned to the same assignee as the present invention, discloses a head clamp having a generally C-shaped frame with a head-engaging pin on one side of the frame and a pair of rotationally adjustable head-engaging pins on an opposing side of the frame. The opposing side of the frame also contains a mechanism for first, adjusting the rotational angular position of the pair of head-engaging pins, and a second, translating or linearly moving the pair of pins with respect to the pin. While the above head clamp works well, it is constructed of nonradiolucent materials. Therefore, use of the above clamp may introduce undesirable artifacts in radiological images taken of a patient with the clamp attached.

Further, radiolucent materials are not well suited for certain components in the adjusting mechanisms of the above clamp design. For example, the head clamp disclosed in the Day, et al. '034 patent uses steel balls which move in and out of detents to move toothed gear rings into and out of engagement thereby respectively locking and unlocking the rotational mechanism. That construction requires very precise dimensional tolerances so that the motion created by the steel balls moving in and out of the detents consistently separates the toothed rings to disengage the teeth on the rings. If those components were made from a plastic-type radiolucent material, the clamping forces would, over time, cause the balls to deform and lose their circular shape. Further, the surfaces in contact with the balls would, over time, form tracks in the ball paths. Either or both of those conditions would eventually result in a loss of dimensional precision that over time would result in inconsistent and unsatisfactory clamp operation.

An example of a known radiolucent clamp is shown in the Day, et al. U.S. Pat. No. 5,276,927, issued to the assignee of the present invention discloses a radiolucent head support with a radiolucent skull clamp secured to the head support. The detailed construction of the head clamp is shown in FIG. 5 herein. Referring to FIG. 5, the radiolucent clamp has a single pin mounted on an adjusting screw 2 at a first end 1 of the clamp. A pair of head-engaging pins are mounted on a clevis 3 which is rotatably mounted in an opposite end 4 the of the head clamp. The clevis 3 is connected to one end of a shaft 5. The opposite end of the shaft contains threads 6 and a locking nut 7. A first toothed member 8 is connected to the clevis 3, and a second tooth member 9 is connected to the opposite end 4 of the head clamp. A compression spring 10 mounted on the shaft 5 between the toothed members 8,9 is used to apply a biasing force tending to separate the toothed members 8,9. In operation, the locking nut 7 is rotated on the threads 6 to move the locking nut 7 away from the opposite end 4 of the clamp. That permits the spring 10 to move the shaft 5 and clevis 3 to the left as illustrated in FIG. 5 thereby separating the toothed members 8,9 and permitting the clevis 3 to freely rotate. When the clevis is moved to its desired angular position, the locking nut 7 is rotated in the opposite direction thereby moving the shaft 5 and clevis 3 to the right as illustrated in FIG. 5 thereby engaging the toothed members 8,9 and locking the clevis 3 in the desired angular position. Thereafter, the adjusting screw 2 at the first end 1 of the clamp is rotated until the patient's head is secured in the clamp.

The above construction has several disadvantages. First, after the patient's head is secured in the clamp, it is difficult to change the angular position of the clevis 3 because the clamping forces applied by the adjusting screw 2 override the biasing force of the spring 10 that is used to separate the toothed members 8,9. Therefore, to change the angular position of the clevis 3, the adjusting screw 2 must be turned to loosen the clamp sufficiently that upon loosening the locking nut 7, the toothed members 8,9 are able to separate. The above mode of operation is less desirable than a design that permits the angular adjustment of the clevis 3 independent of the clamping screw 2. The prior art clamp of FIG. 5 presents a further inconvenience in the bulkiness of the first end 1 of the clamp. Further, applying the clamping force through the single pin on the clamping screw 2, results in less predictable and unequal reactive forces by the pair of pins on the clevis 3.

SUMMARY OF THE INVENTION

To overcome the non-radiolucency of the head clamps referred to above, the present invention provides a radiolucent head clamp wherein all of the adjusting mechanisms are located on a common (single) side of the clamp and are operably connected to the pair of head-engaging pins.

According to the principles of the present invention, the head clamp has a frame with opposing radiolucent first and second frame members forming a generally C-shaped configuration. A first, fixed, head-engaging pin which may be immovable, is mounted on the first frame member. A radiolucent pin holding member is fixed to one end of a radiolucent shaft which is rotatably mounted in the second frame member, and the pin holding member includes a pair of second and third head-engaging pins. The pin holding member is located on a side of the second frame member which faces inwardly, that is, toward the first frame member. A locking mechanism is mounted at the end of the second frame member and is operably connected to the pin holding member for releasably locking the pin holding member in selected angular positions.

The locking mechanism includes a first radiolucent locking member mounted on an outwardly directed side of the second frame member, i.e., that is, opposite the inwardly directed side. The locking mechanism further includes a second radiolucent locking member mounted adjacent the first locking member and moveable with respect thereto. A fastener preferably threaded, and made of radiolucent material, is rotatably mounted to the second frame member adjacent the second locking member such that rotation of the threaded fastener in one direction moves or pushes the locking members into engagement, and rotation of the fastener in the opposite direction permits the locking members to separate.

The invention includes another aspect in which the head clamp has a radiolucent bushing rotatably mounted within the second frame member. The shaft supporting the pin holding member is slidably mounted in the bushing to rotate with the bushing but translate relative thereto. A biasing spring is located between the first and second locking members to bias the second locking member, which is slidably mounted on the bushing, away from the first locking member.

The invention has a further aspect wherein the head clamp has a radiolucent knob rotatably mounted to the other end of the shaft, but slidable with respect to the shaft, and a spring located between the knob and the shaft to limit forces applied to the patient's head by the second and third head-engaging pins.

A head clamp of the above configuration has the advantage of being made of radiolucent materials to minimize artifacts or opaque shadows on radiological images. The radiolucent clamp design provides independent operation of the angular adjustment of the head-engaging pins thereby permitting that angular adjustment without having to loosen the clamp. The radiolucent clamp has the further advantages of providing all of the head-engaging pin position adjustments on the same, single side of the clamp. That design has the advantage of convenience of use, as well as providing a better distribution of clamping forces between the pair of head-engaging pins as the clamp is tightened. In addition, the clamp is made of radiolucent materials which has the advantage of reducing artifacts in images when the clamp is used in radiological applications.

These and other objects and advantages of the present invention will become more readily apparent from the following detailed description and the drawings herein.

DETAILED DESCRIPTION

Figure 1:
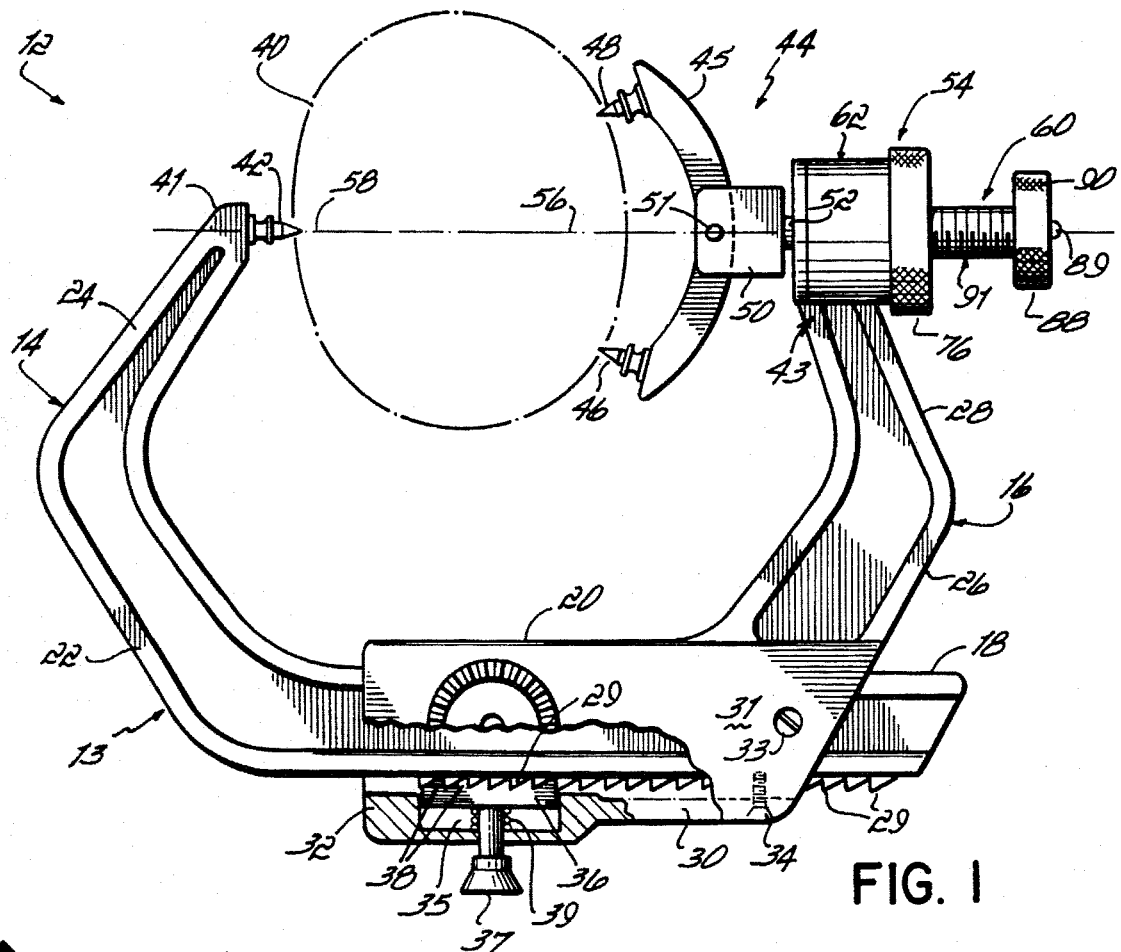
FIG. 1 is a side elevation of a preferred embodiment of the radiolucent surgical head clamp of the present invention showing a patient's head in phantom.

The construction and operation of a preferred form of the surgical head clamp of the present invention will be described with regard to FIGS. 1 through 4. Referring to FIG. 1, the surgical head clamp 12 includes a C-shaped frame 13 comprised of frame members 14 and 16 which are movable to "telescope" toward and away from one another. The frame members 14, 16 of the clamp 12 are preferably made of a of a radiolucent polyethersulfone (PES) and carbon composite material with the carbon component being about 30 percent of the composite by weight. Such a composite material is available from ICI Advanced Materials of Exton, Pa. under the commercial name "THERMOCOMP" JC-1006, and is also available from LNP Engineering Plastics of Thorndale, Pa. under the commercial name "STAT-KON" JC-1006. Alternatively, other radiolucent materials may be used. Frame members 14 and 16 have parallel first arms 18 and 20, respectively, which are juxtaposed to each other in an innerfitting, sliding relationship with first arm 20 of frame member 16 cradling or surrounding the first arm 18 of frame member 14. Extending from one end of the arm 18, frame member 14 has an intermediate arm 22 extending diagonally away from frame member 16 and an upper arm 24 extending angularly back toward frame member 16. Similarly, extending from first arm 20, frame member 16 has an intermediate arm 26 extending away from frame member 14 and an upper arm 28 extending back toward frame member 14. The angled geometry of frame members 14 and 16 maintains frame rigidity and, at the same time, permits the frame members to be physically smaller than if each of the frame members were L-shaped.

The first arm 20 of the frame member 16 is formed in a U-shape to receive the first arm 18 of the frame member 14. The first arm 20 has two sides 30, 31 which extend past the first arm 18. A bottom plate 32 preferably made from the PES and composite material is mounted between the sides 30, 31 of the first arm 20 such that there is clearance between the bottom plate 32 and the rack teeth 29 of the first arm 18. The bottom plate 32 is held in place between the sides 30, 31 of the first arm 20 by fasteners 34, shown in phantom in FIG. 1 and perferably made of nylon. One or more nylon guide pins 33 having teflon tips (not shown) are threaded into the surface 31 so that the teflon tips are in contact with the first arm 18 to help guide the translation of the frame member 14 with respect to frame member 16. The bottom plate 32 has a cavity 35 which is sized to receive a retractable rack member 36 which is connected to a release pin 37. The retractable rack member 36 and release pin 37 are preferably made from the "DELRIN®" acetal polymer material. The retractable rack member 36 has teeth 38 are sized to engage the teeth 29 on first arm 18 of frame member 14. A metal compression spring 39 is mounted over the release pin 37 and extends between the releasable rack member 36 and the bottom plate 32. The compression spring 39 applies a force against the retractable rack 36 which holds the teeth 38 on retractable rack 36 in engagement with teeth 29 on the first arm 18. The engagement of teeth 38,29 prevents the frame members 14,16 from moving in a direction away from each other. However, the configuration of the teeth 38,39 permits frame members 14,16 to be slid toward each other to size or position the clamp 12 generally with respect to a patient's head 40, shown in phantom. To release the clamp, the release pin 37 is pulled downward as illustrated in FIG. 1, thereby compressing spring 39 and moving the teeth 38 of the releasable rack 36 out of engagement with the teeth 29 of the first arm 18. With the teeth 38,29 disengaged, the frame members 14, 16 may be separated thereby releasing the clamp from the patient's head 40.

One end 41 of the clamp 12, that is, the outward extending end of the of frame member 14, preferably has only the minimum size necessary to receive and support a first head-engaging pin 42 which is generally directed toward the frame member 16. Therefore, the end 41 of the clamp 12 presents minimal potential for interference with the surgeon and the operating procedure. An opposite end 43 of the clamp 12, which is the outward extending end of frame member 16, has a radiolucent pin holding member 44. The pin holding member 44 includes a bracket or clevis 45, which may be made from the PES/carbon composite material previously identified. A pair of head-engaging pins, that is, a second head-engaging pin 46 and a third head-engaging pin 48, are mounted proximate the ends of clevis 45 and generally directed toward the first head-engaging pin 42. The patient's head 40 is secured in the clamp 12 by and between the first, second and third head-engaging pins 42,46,48, respectively, which are pressed into opposite sides of the head. The clevis 45 is pivotally mounted in clevis support 50 and may be made from the PES and carbon composite material. The clevis 45 pivots about the centerline of a pivot pin 51 in a plane transverse to the centerline of the pivot pin 51. The pivot pin is made from the radiolucent "DELRIN®" acetal polymer material. A rod, or shaft 52, for example, made from a radiolucent "TORLON" polyamide-imide material has one end connected to the clevis support 50 by a radiolucent nylon screw 53 which extends through the clevis support 50 and is threaded into a threaded center hole of the shaft 52 (see FIGS. 2 and 3).

The clamp 12 includes an angular positioning mechanism 54 for releasably locking the pin holding clevis 45 in selected angular (rotational) positions around an axis of rotation 56 which is approximately coincident with a centerline 58 of pin 42 and preferably passes through the centerline of pivot pin 51. The clamp also includes a translation or adjusting mechanism 60 for linearly (axially) moving the pin holding member longitudinally along the axis of rotation 56.

Figure 3:
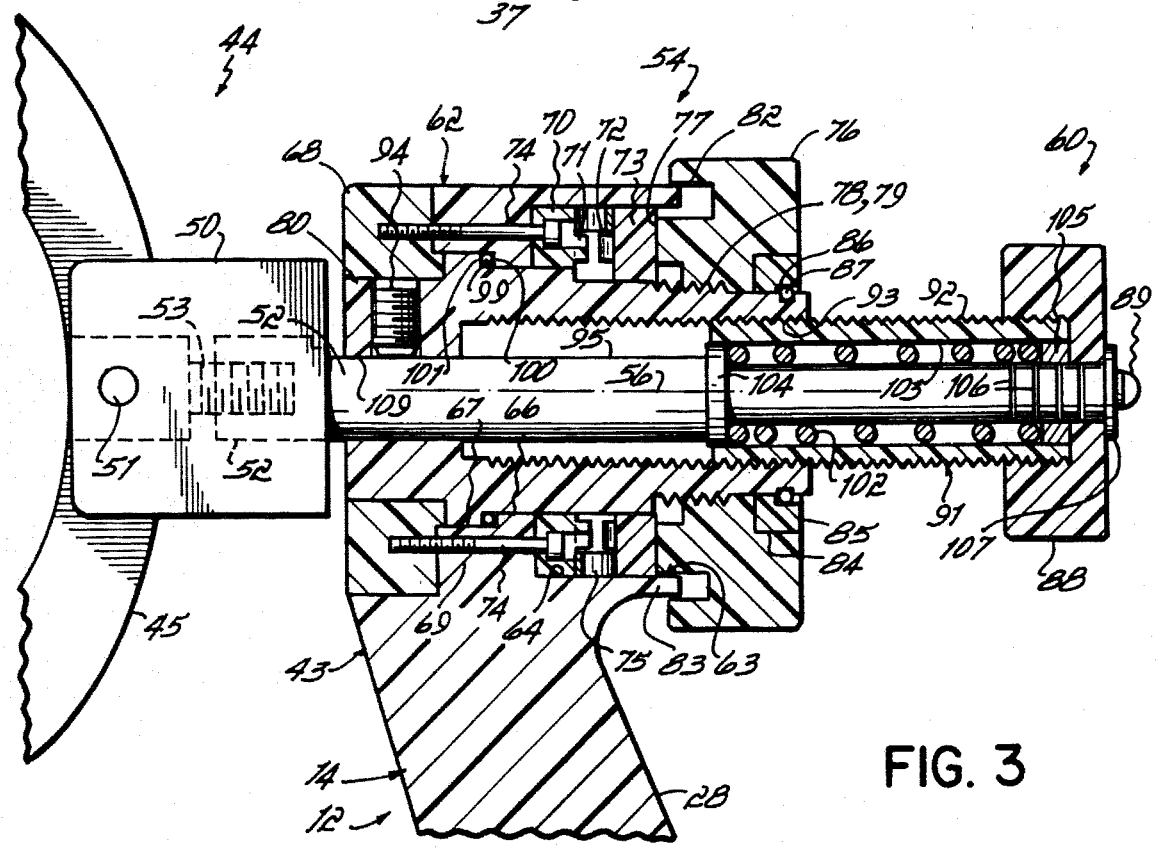
FIG. 3 is an enlarged axial cross-sectional view of the radiolucent pin adjusting mechanism, illustrating the radiolucent angular position locking mechanism in the disengaged or unlocked position.
Figure 2:
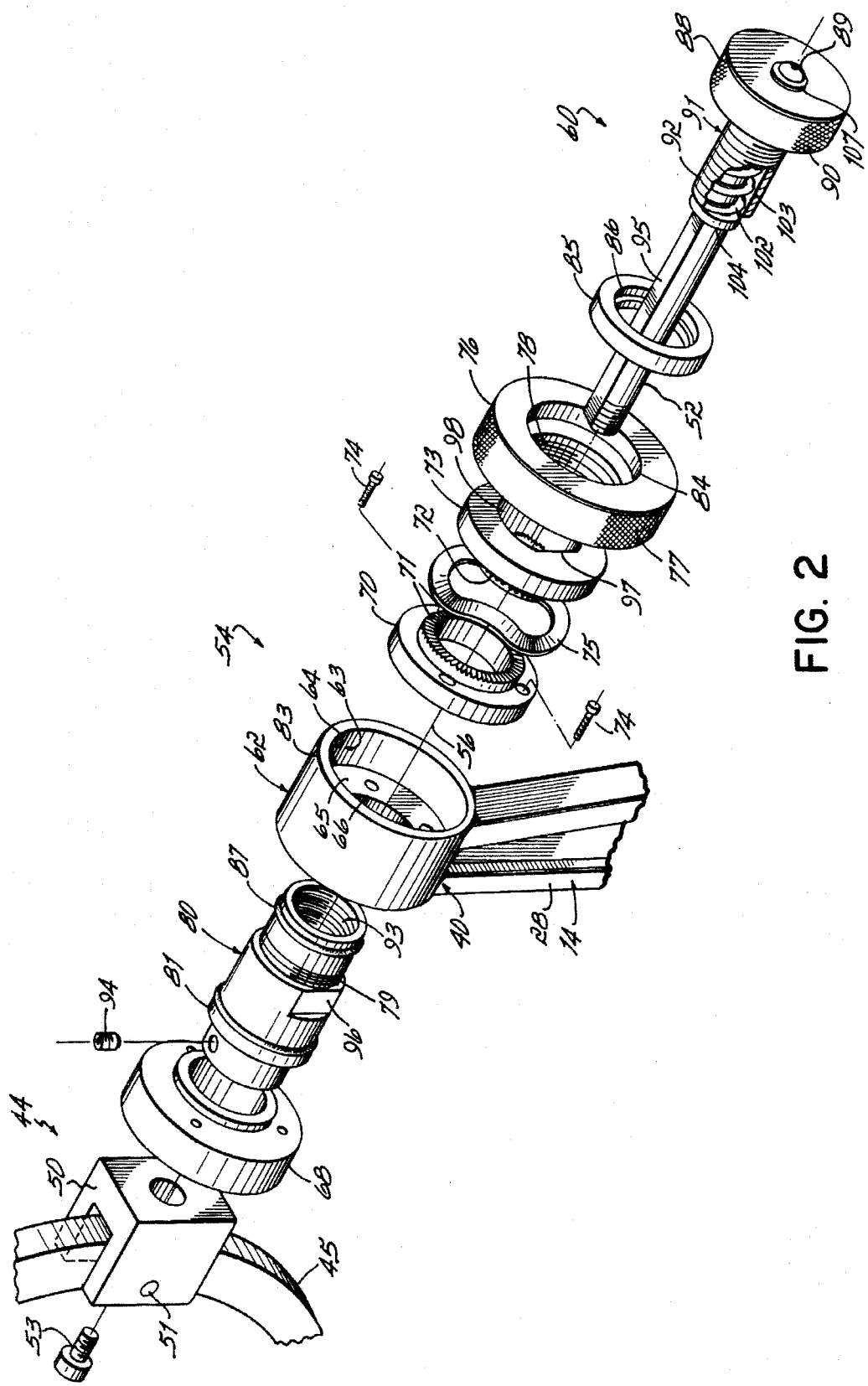
FIG. 2 is an exploded perspective view of the radiolucent pin rotating, translating, and locking mechanism of a surgical head clamp in accordance with a preferred embodiment of the invention.

As best shown in FIG. 2, a generally cylindrical body portion on member 62 is formed on the outwardly extending end of the upper arm 28 at the end 43 of the clamp 12. The body member 62 has a stepped bore 63 which has a first bore 64 with a layer first diameter that terminates at a shoulder or flange 65 within the stepped bore 63, and the stepped bore 63 has a centerline that is coincident with the axis of rotation 56. The stepped bore 63 extends past the flange 65 and has a second bore 66 concentric with the first bore 64. As shown in FIG. 3, the stepped bore 63 has a third bore 67 on the other side of the flange 65 which is concentric with the first and second bores 63,64 and is sized to receive a closure or cap 68 made from the radiolucent "DELRIN®" acetal polymer material.

Referring back to FIG. 2, the angular positioning mechanism 54 comprises a first locking ring 70 having interlocking means preferably in the form of toothed ring 71 on a first end face thereof, which is engagable with a mating toothed ring 72 of a second locking ring 73. Applicant has found that when two pieces of PES and carbon material as specified herein are in sliding contact with each other, there is an abrading action that takes place between the two parts. That abrading action results in an undesirable dust or particles of the material collecting on other components of the clamp. The quantity of undesirable abraded particles can be reduced by manufacturing the two parts from dissimilar materials. Therefore, the locking ring 70 is made from the radiolucent PES and carbon composite material, and locking ring 73 is preferably made from the radiolucent "DELRIN®" acetal polymer material. The first bore 64 is sized to receive locking rings 70,73 and maintains the locking rings 70,73 in coaxial alignment as the locking ring 73 is moved longitudinally in the bore 64 with respect to the locking ring 70. The first locking ring 70 is immovably secured against the flange 65 such that the first end face and toothed ring 71 face in a direction away from the first frame member 14, and the toothed ring 72 of second locking member 73 faces in a direction toward the first frame member 14. Screws 74 made of nylon or other radiolucent material extend through holes in the first locking ring 70, through holes in the flange 65 of the cylindrical body member 62 and are secured in the cap 68, thereby securing the first locking ring 70 and the cap 68 to opposite sides of the flange 65 of the cylindrical body member 62. A wave washer, or corrugated spring 75 is located between the locking rings 70,73 and surrounds toothed rings 71,72. When compressed, the spring 75 produces a force in a direction tending to push the locking rings 70,73 apart, thereby separating the toothed rings 71,72 from interlocking engagement.

A knob or ring 76 made of the radiolucent "DELRIN®" acetal polymer material is mounted such that an end surface 77 is in sliding contact with the second locking member 73. The knob 76, functioning as a manually operable actuator, is joined to a rotator sleeve 80 by a mechanical coupling, preferably, internal threads interlocking with external threads 79 of the sleeve 80. The rotator sleeve 80 is a cylindrical bushing which is made from the earlier described PES and carbon composite material. The rotator sleeve is rotatably mounted within the body member 62 so that its centerline is collinear with the axis of rotation 56. An annular flange 81 on the rotator sleeve 80 is sized to mate with and rotatably slides within the third bore 67, and the second bore 66 is sized to mate with and rotatably slide about an outer cylindrical surface of the rotator sleeve 80. Referring to FIG. 3, the knob 76 has an annular groove 82 in one face which is sized to receive the side wall, or face, 83 of the body member 62. The knob 76 has a bore 84 at an opposite end, and a cylindrical keeper 85 which functions to limit motion of the knob 76 is press fit or otherwise secured within the bore 84. The keeper 85 is made from the radiolucent "DELRIN®" acetal polymer material and has a bore 86 which is sized to slide snugly over a "BUNA" nitrile elastomer O-ring 87 which is mounted on the end of the rotator sleeve 80.

Independent longitudinal (axial) motion of the pin holding member 44 is generated by a translation mechanism 60. The shaft 52 is slidably mounted within the rotator sleeve 80 such that the centerline of the shaft is collinear with the axis of rotation 56. An operating handle, or knob 88 includes a knurled member 90 made from the radiolucent "DELRIN®" acetal polymer material and a threaded sleeve, or threaded tube 91 made of "TORLON" polyamide-Imide. "TORLON" polyamide-Imide is a desirable material because it is commercially available in rod form, thereby reducing machining costs. The member 90 has a bore which is threaded onto one end of a external cylindrical surface 92 of the tube 91. The other end of the threaded external surface 92 of the threaded tube 91 is coupled with an internal threaded bore 93 of the rotator sleeve 80, thereby rotatably coupling the knob 88 to the rotator sleeve 80. The opposite end of the shaft 52 extends through the center of and is slidable with respect to of the knob 88. A stainless steel screw 89 is threaded into the opposite end of the shaft 52 and a stainless steel bearing washer 107 limits the linear motion of the shaft 52 in one direction with respect to the knob 88.

The rotator sleeve 80 has a cross-sectional shape that includes a flat surface 109 that mates with the cross-sectional shape of shaft 52 that includes the flat surface 95. Their mating cross-sectional shapes spline, or key, the rotator sleeve 80 and to the shaft 52 and prevent relative rotation between the rotator 80 and the shaft 52 but allow them to translate, or slide, relative to each other. Unitary rotation of the rotator 80 and the shaft 52 is further provided by a nylon set screw 94 radially threaded into the rotator 80 and slidably engaging the flat surface 95 on the shaft 52. The rotator sleeve 80 extends through a bore in the first locking ring 70 and is free to rotate with respect to the first locking ring 70. However, a flat surface 96 at one end of the sleeve 80 cooperates with a flat surface 97 within an axial bore 98 of the second locking ring 73 so that the second locking ring 73 slides with respect to the rotator sleeve 80, but second locking ring 73 and the rotator sleeve 80 rotate in unison.

In use, the angular positioning mechanism 54 is operated to adjust the angular position of the clevis 45 and the head-engaging pins 46,48 about the axis 56 independently of the operation of the translating mechanism 60 and independently of whether the clamp is supporting a patient's head 40. To change the angular position of the clevis 45, the knob 76 is rotated in a first, or loosening, direction, for example, a counterclockwise direction, relative to the rotator sleeve 80. The knob 76 backs away (to the right as viewed in FIG. 3), and the corrugated spring 75 exerts a force against the second locking ring 73, thereby moving the second locking ring 73 to the right away from the first locking ring 70 and away from the first frame member 14 until the respective toothed rings 71,72 disengage. As the knob 76 is rotated in the first direction, the keeper 85 slides over the O-ring 87 until the O-ring 87 contacts the bottom surface of the bore 86 within the keeper 85. At that point, resistance to further rotation of the knob in the first direction is encountered by the user, thereby signaling the user that the toothed rings are disengaged and to stop rotating the knob 76. The user may then manually rotate the clevis 45 which causes the head 40, clevis 45, support member 50, shaft 52, rotator sleeve 80 and second locking ring 73 to rotate in unison. As the head clamp is being tightened, clamping forces parallel to the axis of rotation 56 are applied against the clevis 45 which will tend to move the flange 81 toward and against the flange 65. An low friction O-ring 99 made of "TEFLON®" polytetrafluoroethylene is located between a bearing surface 100 on a side of the flange 65 of the body member 62 and a bearing surface 101 on a side of the flange 81 of the rotator sleeve 80. The O-ring 99 is used to reduce the friction between the surfaces 100, 101 when the clevis 45 is rotated to change its angular position; and the clamping force is transmitted across the bearing surfaces 100,101 by the O-ring 99. The O-ring 99 and flange 81 are captured between the flange 65 and an end surface of the cap 68 which is effective to hold the rotator sleeve in its desired longitudinal position.

Figure 4:
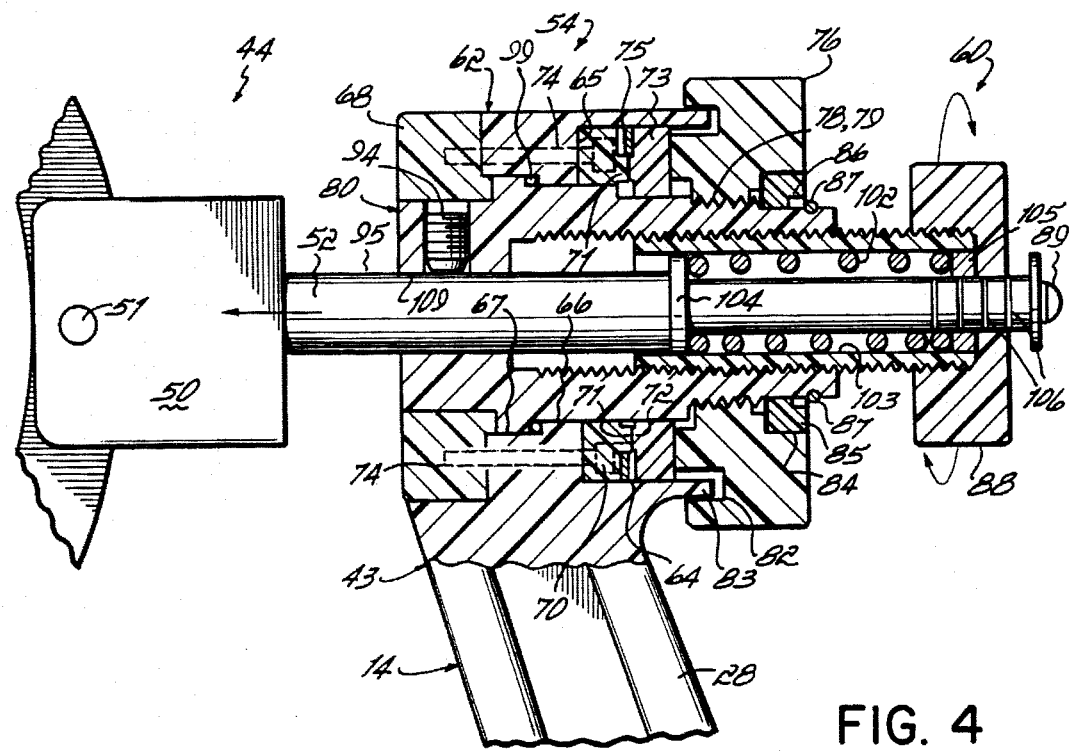
FIG. 4 is an axial cross-sectional view similar to FIG. 3 but illustrates the radiolucent angular position locking mechanism in its engaged or locked position.

When the desired angular position is achieved, the knob 76 is rotated in an opposite second, or locking, direction, for example, a clockwise direction, and the knob 76 moves to the left relative to the sleeve 80 as viewed in FIG. 4. Continued rotation of the knob 76 in the second direction causes the knob 76 to push the second locking ring 73 toward the first locking ring 70 and the first frame member 14 until the respective toothed rings 71, 72 contact each other and reach a fully engaged position. When the toothed rings 71, 72 contact each other, the user experiences in increased resistance to rotation which signals the user that the toothed rings are engaged, and the clevis 45 is locked in the desired position. With the second locking ring 73 locked from rotational motion with respect to the first locking ring 70, the rotator sleeve 80 is prevented from relative rotation with respect to the second locking ring 73 by means of the flat 96 on the sleeve 80 and the mating flat 97 on the second locking ring 73 (FIG. 2). Further, since the shaft 52 cannot rotate relative to the sleeve 80, the meshed toothed rings 71,72 are effective to prevent the clevis 45 from rotating.

The knob 76 threadedly mounted on the end of sleeve 80 functions as a manually operable actuator that is mechanically coupled to the sleeve 80. The mechanical coupling, for example, the interlocking threads on the knob 76 and sleeve 80 move the knob 76 away from the first end 41 of the frame member 14 in response to rotation of the knob 76 in a first direction, thereby allowing the toothed members 71, 72 to separate. The mechanical coupling between the knob 76 and sleeve 80 moves the knob, or actuator, 76 toward the first end 41 of the frame member 14 in response to rotation of the actuator 76 in the opposite direction, thereby moving the toothed rings 71, 72 into engagement.

The translation mechanism 60 is used to change the position of the clevis 45 and head-engaging pins 46,48 with respect to the head-engaging pin 42 by rotating the knob 88. Rotation of the knob 88 in a first direction, for example, a clockwise direction, advances the shaft 52 with respect to sleeve 80 and causes the knob 88, shaft 52 and pin holding member 44 to translate along the axis of rotation toward the first head-engaging pin 42. Therefore, the pin holding member 44 is linearly adjusted with respect to the first pin 42 independently of the operation and state of engagement of the angular position mechanism 54, that is, whether the angular locking mechanism 54 is in its locked or unlocked position.

A helical compression spring 102 is located within a bore 103 of the threaded tube 91 and extends over and about the shaft 52. The spring 102 is located between a shoulder of a flange 104 on the shaft 52 and a bearing washer 105 adjacent the knurled member 90. The flange 104 has a diameter such that the flange 104 contacts the side wall of the bore 103 at the outer directed end of the threaded tube 91, thereby providing diametric support for the threaded tube 91 at its outer directed end. The spring 102 permits the surgeon to measure and control the forces applied by the second and third head-engaging pins 46, 48 to the patient's head 40. After the pins contact the head, continued rotation of the knob 88 will result in continued translation of the shaft 52 and pin holding member 44 which is effective to compress the spring 102. With further rotation of the knob 88, the spring 102 continues to compress; and the shaft 52 extends beyond the knob 88, i.e., to the right, as shown in FIG. 4. Therefore, the force applied to the patient's head 40 by the head-engaging pins is determined by the spring constant of the spring 102. The shaft 52 contains a scale, or markings, 106 so that the clamping force may be controlled by the surgeon. Typically, each line on the scale 104 represents about 20 pounds of force.

Figure 5:
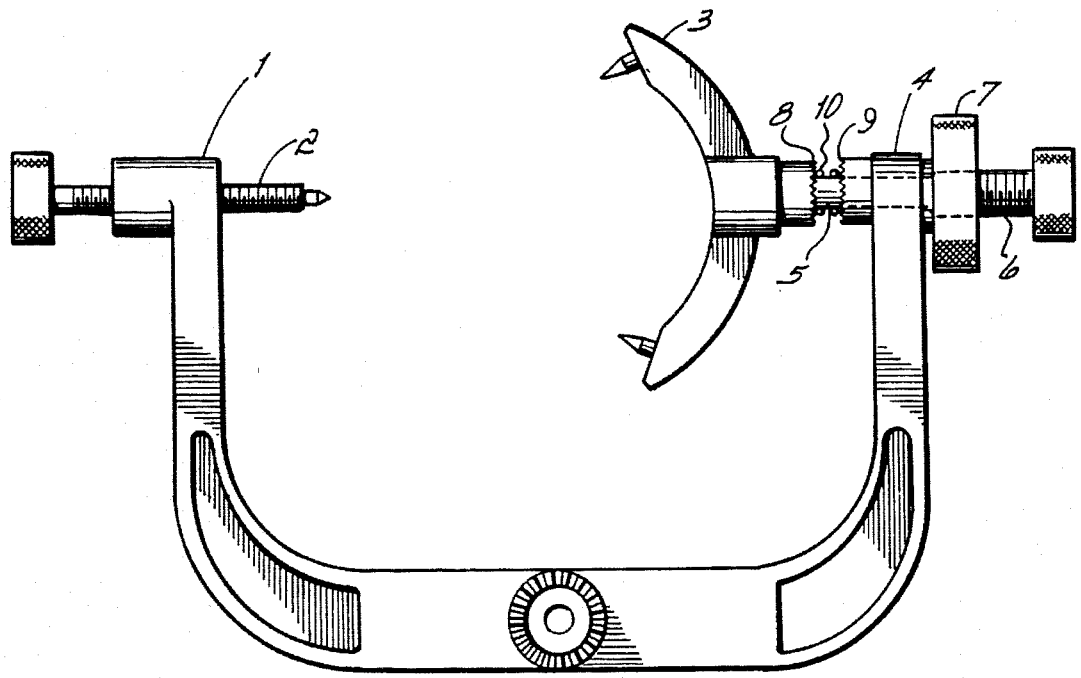
FIG. 5 is a side elevation of the prior art radiolucent head clamp shown in Day, U.S. Pat. No. 5,276,927.

The head clamp of the construction described above may be used in surgical applications and will result in few if any undesirable artifacts or opaque shadows when used in radiological applications. The disclosed invention is especially useful when radiological imagery is used during and to assist surgical procedures. The design described herein provides a radiolucent head clamp having an angular head positioning adjustment which can be operated without having to loosen the clamp, as is required by the prior art illustrated in FIG. 5. Further, the radiolucent head clamp of the present invention has one end 42 which is minimal in size, and further has all of the clamp adjustments conveniently located together at the other end 43 of the head clamp 12. This again provides a more convenient operation than the design of the prior art illustrated in FIG. 5. Further, the individual components of the head clamp of the present invention may be made of radiolucent materials and withstand the clamping forces and other forces encountered in use better than the components utilized in the clamp illustrated in the Day, et al. U.S. Pat. No. 5,269,034 if those components were made of radiolucent materials. The design provides a radiolucent clamp having one end 41 which is of minimal size, and wherein all of the clamp adjustments are conveniently located together at the other end 43 of the clamp 12.

While the present invention has been set forth by a description of an embodiment in considerable detail, it is not intended to restrict or in any way limit the claims to such detail. Additional advantages and modifications will readily appear to those who are skilled in the art. For example, the generally cylindrical body member 62 may be a separate piece which is mechanically attached or bonded to the outward extending end of the frame member 16. Further, the body member 62 may be made from a radiolucent "DELRIN®" acetal polymer material or other radiolucent material. In addition, different radiolucent materials may be used in place of those identified above. For example, the cap 68 may be made from the PES and carbon composite material. Further, variations may be made to the above described constructions. For example, the shaft 52 may be fitted into the rotator sleeve 80 with sufficient precision that the set screw 94 is not required. Further, the actuator knob 76 may be coupled to the sleeve 80 by another mechanism such that actuation of the coupling with respect to the sleeve 80 is operable to move the actuator and either separate or engage the toothed rings 71,72. Alternatively, the cylindrical body member 62 and the end of the frame member 14 may be configured with a mating mechanical coupling, such as a dove tail configuration, and those members may be mechanically coupled with or without a bonding material. The invention in its broadest aspects is therefore not limited to the specific details shown and described. Accordingly, departures may be made from such details without departing from the spirit and scope of the invention.

What is claimed is:

1. A head clamp for supporting a patient's head comprising:
   a frame having first and second frame members;
   a first head-engaging pin mounted on one end of the first frame member and directed toward the second frame member;
   a pin holding member rotatably mounted on one end of the second frame member, the pin holding member including second and third head-engaging pins generally directed toward the first head-engaging pin, and
   an angular positioning mechanism mounted at the one end of the second frame member and operably connected to said pin holding member for releasably locking said pin holding member in selected angular positions with respect to an axis of rotation of the pin holding member, the angular positioning mechanism including
   a first locking member connected to the one end of the second frame member,
   a second locking member slidably mounted at the one end of the second frame member adjacent the first locking member and engaging the first locking member in response to the second locking member being moved toward the first frame member, the second locking member disengaging the first locking member in response to being moved away the first frame member,
   a sleeve rotatably mounted within the one end of the second frame member with a centerline of the sleeve substantially collinear with the axis of rotation of the pin holding member;
   a shaft extending through the second frame member and having one end connected to the pin holding member, the shaft being mounted within the sleeve to rotate with the sleeve;
   a manually operable actuator being threadedly coupled to one end of the sleeve, the actuator moving the second locking member toward the first frame member in response to being rotated in a first direction, thereby locking the pin holding member in an angular position, and the actuator permitting the second locking member to move away from the first frame member in response to the actuator being rotated in a second direction, thereby permitting the pin holding member to rotate with respect to the second frame member.

2. The head clamp of claim 1 wherein the one end of the sleeve comprises an annular ring and the actuator includes a bore on one end sized to receive the annular ring whereby the annular ring contacts a surface of the bore in response to rotation of the actuator in the opposite rotational direction, thereby limiting motion of the actuator in the opposite rotational direction.

3. The head clamp of claim 1 wherein the one end of the second frame member including a first flange member extending toward the sleeve and the sleeve further including a second flange member extending adjacent the first flange member, and the head clamp further comprising an annular low friction bearing member in contact with the first and second flange members for facilitating relative rotational motion between the first and second flanges.

4. The head clamp of claim 1 further comprising a spring member located between the first and second locking members to apply a force against the second locking member to push the second locking member away from the first locking member and the first frame member.

5. The head clamp of claim 4 wherein the second locking member is slidably mounted on the sleeve to rotate with the sleeve and translate in a longitudinal direction with respect to the sleeve.

6. The head clamp of claim 5 wherein the first and second locking members and the spring member are located within a bore on the second frame member and wherein further the actuator is threadedly connected to an outer directed surface of the one end of the sleeve and the actuator has an annular projection extending into the bore and in contact with the second locking member.

7. The head clamp of claim 6 wherein the shaft is slidably mounted within the sleeve to slide longitudinally with respect to the sleeve, and wherein further the head clamp includes a knob rotatably connected to an opposite end of the shaft and the knob includes a sleeve threadedly connected to an inner directed circumferential surface of the sleeve, whereby rotation of the knob thereby translates the second and third head-engaging pins with respect to the first head-engaging pin.

8. The head clamp of claim 7 wherein the knob is slidably connected to the shaft and the shaft translates with respect to the knob in response to the head-engaging pins engaging a head and the knob is rotated to move the second and third head-engaging pins toward the first head-engaging pin and the head clamp further comprising a spring located with respect to the knob and the shaft to limit the forces applied to the patient's head by said second and third head-engaging pins in response to continued rotation of the knob to move the second and third head-engaging pins toward the first head-engaging pin.

9. The head clamp of claim 8 wherein the frame members, the pin holding member, the locking mechanism, the sleeve, the shaft and the knob are made from radiolucent materials.

10. A head clamp for supporting a patient's head comprising:
    a first frame member including a first head-engaging pin mounted on one end of the first frame member;
    a second frame member having one end with a mounting bore having a central axis substantially collinear with a central axis of the first head-engaging pin;
    a sleeve rotatably mounted in the mounting bore of the second frame member;
    a shaft centrally slidably mounted within the sleeve and coupled to the sleeve to rotate with the sleeve;
    a pin holding member connected to one end of the shaft and including second and third head-engaging pins generally directed toward the first head-engaging pin, the pin holding member having an axis of rotation collinear with the central axis of the first head-engaging pin;

a first locking member located within the mounting bore and connected to the second frame member, the first locking member having a central bore for receiving the sleeve, the sleeve being rotatable with respect to the first locking member;

a second locking member slidably mounted within the mounting bore and movable toward and away from the first locking member, the second locking member being slidable with respect to the sleeve and coupled to the sleeve to rotate in unison with the sleeve; and a knob threadedly connected mounted on the one end of the sleeve and having an end surface in direct sliding contact with the second locking member, the knob moving the second locking member into locking engagement with the first locking member in response to rotation of the knob in one rotational direction, thereby locking the pin holding member in a desired angular position, and the knob permitting the second locking member to separate from the first locking member in response to rotation of the knob in an opposite rotational direction, thereby permitting the pin holding member to rotate with respect to the second frame member.

* * * * *